United States Patent

Petitpierre

[11] 4,089,546
[45] May 16, 1978

[54] PRESSURE-SENSITIVE AND/OR HEAT-SENSITIVE RECORDING MATERIAL

[75] Inventor: Jean Claude Petitpierre, Kaiseraugst, Switzerland

[73] Assignee: CIBA-GEIGY Corporation, Ardsley, N.Y.

[21] Appl. No.: 748,869

[22] Filed: Dec. 9, 1976

[30] Foreign Application Priority Data

Dec. 17, 1975 Switzerland .................. 16339/75

[51] Int. Cl.² .................. B41M 5/16; B41M 5/18; B41M 5/22
[52] U.S. Cl. .................. 282/27.5; 427/150; 427/151; 428/323; 428/411; 428/537; 428/913; 428/914
[58] Field of Search .......... 282/27.5; 427/146, 150, 427/151, 152, 153; 428/327, 411, 537, 913, 914, 323

[56] References Cited

U.S. PATENT DOCUMENTS

| | | | |
|---|---|---|---|
| 2,025,089 | 5/1977 | Garner et al. | 282/27.5 |
| 3,076,721 | 2/1963 | Coles et al. | 428/913 X |
| 3,149,990 | 9/1964 | Coles et al. | 428/913 X |

Primary Examiner—Thomas J. Herbert, Jr.
Assistant Examiner—Bruce H. Hess
Attorney, Agent, or Firm—Edward McC. Roberts; Prabodh I. Almaula

[57] ABSTRACT

A pressure-sensitive and/or heat-sensitive recording material which contains, as the color former, at least one azine compound of the general formula $$A-CH=N-N=CH-A \qquad (1)$$

in which A represents one of the following radicals

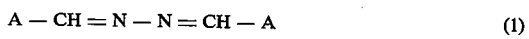

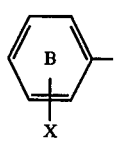

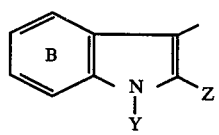

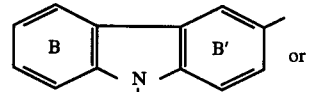

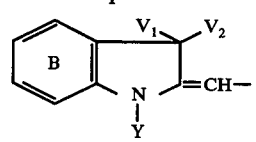

wherein
X denotes the radical

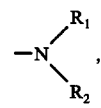

$-O-R_1$ or $-S-R_1$, $R_1$ denotes alkyl which has at most 12 carbon atoms and is unsubstituted or substituted by halogen, hydroxyl, cyano, lower alkoxy or lower alkoxy-carbonyl, cycloalkyl or phenyl or benzyl which are unsubstituted or substituted by halogen, nitro, lower alkyl or lower alkoxy, $R_2$ denotes hydrogen, alkyl which has at most 12 carbon atoms and is unsubstituted or substituted by halogen, hydroxyl, cyano, lower alkoxy or lower alkoxycarbonyl, cycloalkyl or benzyl which is unsubstituted or substituted by halogen, nitro, lower alkyl or lower alkoxy, or $R_1$ and $R_2$ together with the nitrogen atoms which links them denote a 5-membered or 6-membered heterocyclic radical, Y denotes hydrogen, alkyl which has at most 12 carbon atoms and is unsubstituted or substituted by halogen, hydroxyl, cyano, lower alkoxy or lower alkoxy-carbonyl, or benzyl which is unsubstituted or substituted by halogen, nitro, lower alkyl or lower alkoxy, Z denotes hydrogen, lower alkyl or phenyl and $V_1$ and $V_2$ each denote lower alkyl, cycloalkyl or benzyl, or conjointly denote alkylene, and the rings B and B' independently of one another can be further substituted by halogen, nitro, cyano, trifluoromethyl, lower alkyl, lower alkoxy, lower alkoxy-carbonyl, phenoxy, amino, lower alkylamino or N-lower alkyl-carbonylamino.

15 Claims, No Drawings

PRESSURE-SENSITIVE AND/OR HEAT-SENSITIVE RECORDING MATERIAL

The present invention relates to pressure-sensitive or heat-sensitive recording material which contains, as the colour-forming agent in its colour-forming system, at least one azine compound of the general formula $$A - CH = N - N = CH - A \qquad (1)$$

in which A represents one of the following radicals

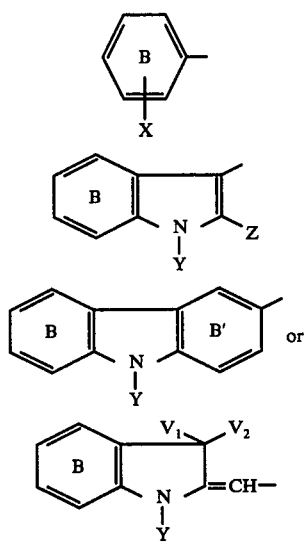

in which X denotes the radical

—O—$R_1$ or —S—$R_1$, $R_1$ denotes alkyl which has at most 12 carbon atoms and is unsubstituted or substituted by halogen, hydroxyl, cyano, lower alkoxy or lower alkoxy-carbonyl, cycloalkyl with, preferably, 5 or 6 carbon atoms, or phenyl or benzyl which are unsubstituted or substituted by halogen, nitro, lower alkyl or lower alkoxy, $R_2$ denotes hydrogen, alkyl which has at most 12 carbon atoms and is unsubstituted or substituted by halogen, hydroxyl, cyano, lower alkoxy or lower alkoxy-carbonyl, cycloalkyl with, preferably, 5 or 6 carbon atoms or benzyl which is unsubstituted or substituted by halogen, nitro, lower alkyl or lower alkoxy, or $R_1$ and $R_2$ together with the nitrogen atom which links them denote a 5-membered or 6-membered, preferably saturated, heterocyclic radical, Y denotes hydrogen, alkyl which has at most 12 carbon atoms and is unsubstituted or substituted by halogen, hydroxyl, cyano, lower alkoxy or lower alkoxy-carbonyl, or benzyl which is unsubstituted or substituted by halogen, nitro, lower alkyl or lower alkoxy, Z denotes hydrogen, lower alkyl or phenyl and $V_1$ and $V_2$ each denote lower alkyl, cycloalkyl or benzyl, or conjointly denote alkylene, and the rings B and B' independently of one another can be further substituted by halogen, nitro, cyano, trifluoromethyl, lower alkyl, lower alkoxy, lower alkoxy-carbonyl, phenoxy, amino, lower alkylamino or N-lower alkyl-carbonylamino.

Amongst the azine compounds of the formula (1), those in which the two A's represent a radical of the formula (1.1), in which X denotes an amino group

are preferred. In the formula (1.1), the substituent X is preferably in the p-position. However, it can also be in the o-position and m-position.

In the definition of the radicals of the azine compounds, lower alkyl and lower alkoxy as a rule represent those groups or constituents of groups which contain 1 to 5, and especially 1 to 3, carbon atoms, such as, for example, methyl, ethyl, n-propyl, isopropyl, n-butyl, sec.-butyl or amyl and, respectively, methoxy, ethoxy or isopropoxy.

If the substituents $R_1$, $R_2$ and Y represent alkyl groups, they can be straight-chain or branched alkyl radicals. Examples of such alkyl radicals are methyl, ethyl, n-propyl, isopropyl, n-butyl, sec.-butyl, n-hexyl, n-octyl or n-dodecyl.

If the alkyl radicals in $R_1$, $R_2$ and Y are substituted they are, above all, cyanoalkyl, halogenoalkyl, hydroxyalkyl or alkoxyalkyl, with 2 to 4 carbon atoms in each case, such as, for example, β-cyanoethyl, β-chloroethyl, β-hydroxyethyl, β-methoxyethyl or β-ethoxyethyl.

Examples of cycloalkyl in the meaning of the R and V radicals are cyclopentyl or, preferably, cyclohexyl.

Examples of preferred substituents in the benzyl group of the R and Y radicals and in the phenyl group of $R_1$ are halogens, nitro, methyl or methoxy. Examples of such araliphatic and aromatic radicals are p-methylbenzyl, o- or p-chlorobenzyl, o- or p-nitrobenzyl, o- or p-tolyl, xylyl, o-, m- or p-chlorophenyl or o- or p-nitrophenyl.

If the substituents $R_1$ and $R_2$, together with the common nitrogen atom, represent a heterocyclic radical, the latter is, for example, pyrrolidino, piperidino, pipecolino, morpholino, thiomorpholino or piperazino.

The substituents $R_1$ and $R_2$ are preferably benzyl or lower alkyl. The N-substituent Y is, in particular, benzyl or alkyl with 1 to 8 carbon atoms, for example n-octyl or, above all, methyl or ethyl.

The radicals $V_1$ and $V_2$ can differ from one another or are preferably identical.

$V_1$ and $V_2$ preferably denote lower alkyl and above all they both denote methyl. If $V_1$ and $V_2$ together denote alkylene, they preferably contain 4 or 5 carbon atoms and form, together with the carbon atom which links them, a cyclopentane or cyclohexane ring.

The rings B and B' are preferably not further substituted or are further substituted by halogen or lower alkoxy, for example by chlorine or methoxy.

Colour-forming agents comprising azine compounds of the formula (1) which are important in practice correspond to the general formula $$A_1 - CH = N - N = CH - A_1 \qquad (2)$$

in which $A_1$ represents one of the following radicals

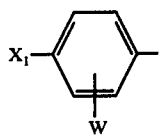 (2.1)

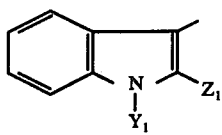 (2.2)

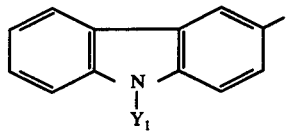 or (2.3)

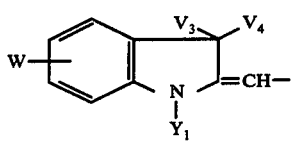

(2.4)

in which $X_1$ denotes the radical

,

—O—$R_3$ or —S—$R_3$, $R_3$ and $R_4$ independently of one another denote lower alkyl or benzyl which is unsubstituted or substituted by halogen, nitro, methyl or methoxy, $Y_1$ denotes alkyl with 1 to 8 carbon atoms, preferably methyl or ethyl, or benzyl which is unsubstituted or substituted by halogen, nitro, methyl or methoxy, $Z_1$ denotes lower alkyl, above all methyl, or phenyl, $V_3$ and $V_4$ each denote lower alkyl, above all methyl, and W denotes hydrogen, halogen, lower alkyl, such as, for example, methyl, or lower alkoxy, such as, for example, methoxy.

In connection with the above substituents in the formulae (1) and (2), halogen is, for example, fluorine, bromine or, preferably, chlorine.

Preferred colour-forming agents correspond to the general formula $$A_2 - CH = N - N = CH - A_2 \qquad (3)$$

in which $A_2$ represents one of the following radicals

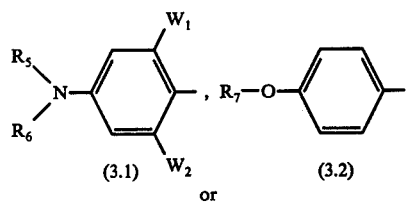

or

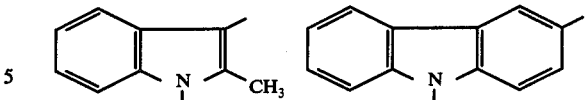

(3.3)    (3.4)

in which $R_5$ denotes lower alkyl, hydroxy-lower alkyl, chloro-lower alkyl, benzyl, phenyl or methoxyphenyl, $R_6$ denotes lower alkyl, hydroxy-lower alkyl, chloro-lower alkyl or benzyl, or $R_5$ and $R_6$, together with the nitrogen atom which links them, denote pyrrolidino, piperidino or morpholino, $R_7$ denotes lower alkyl, $W_1$ and $W_2$ each denote hydrogen, chlorine or methyl, $Y_2$ denotes alkyl with 1 to 8 carbon atoms or benzyl and $Y_3$ denotes lower alkyl.

Particularly valuable colour-forming agents in the colour-forming system of the recording material according to the invention are azine compounds of the general formula

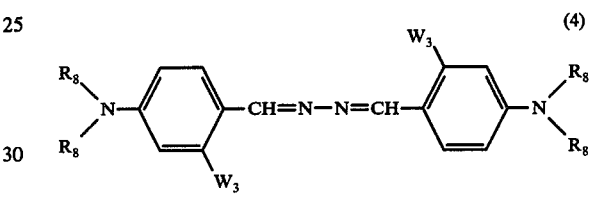 (4)

in which $R_8$ denotes lower alkyl or benzyl and $W_3$ denotes hydrogen or methyl.

Amongst these compounds of the formula (4), those in which all the $R_8$ denote methyl or ethyl are preferred.

The azine compounds of the formulae (1) to (4) are known in some cases but are a new category of colour-forming agents. They can be manufactured according to processes which are in themselves known. For example, they can be manufactured by subjecting 2 mols of an aldehyde compound of the formula

A — CHO in which A has the indicated meaning, to a condensation reaction with 1 mol of hydrazine hydrate. The reaction is appropriately carried out in a polar organic solvent, especially in lower alcohols, such as, for example, methanol or ethanol, and preferably in the presence of a catalyst, such as, for example, glacial acetic acid or a tertiary amine. The reaction can be carried out even at room temperature (20° to 25° C). However, it is appropriate to use elevated temperature, preferably 40° to 80° C.

The azine compounds of the formulae (1) to (4) are usually colourless or at most slightly coloured. When these colour-forming agents are brought into contact with an acid developer, that is to say an electron acceptor, they give yellow, orange or red colour shades which are outstandingly fast to light. They are therefore also very valuable when mixed with other known colour-forming agents, for example crystal violet lactone, 3,3-(bis-aminophenyl)-phthalides, 3-(aminophenyl-3-indolyl)-phthalides, 2,6-diaminofluoranes or benzoyl-leucomethylene blue, in order to give blue, navy blue, grey or black colorations.

These colour-forming agents are suitable above all for use in a pressure-sensitive or heat-sensitive recording material, which can be copying material and also documenting material.

A pressure-sensitive material comprises, for example, at least one pair of sheets which contain at least one colour-forming agent of the formulae (1) to (4) dissolved in an organic solvent, and an electron acceptor substance as the developer. The colour-forming agent gives a coloured marking at the points at which it comes into contact with the electron acceptor substance.

Typical examples of such developers are attapulgite clay, silton clay, silicon dioxide, bentonite, halloysite, aluminium oxide, aluminium sulphate, aluminium phosphate, zinc chloride, kaolin or any other desired clay or a polymeric material having an acid reaction, such as, for example, a phenolic polymer, an alkylphenol-acetylene resin, a maleic acid/rosin resin or a partially or completely hydrolysed polymer of maleic anhydride with styrene, ethylene, vinyl methyl ether or carboxypolymethylene. Attapulgite clay, silton clay or a phenol-formaldehyde resin are preferred developers.

These electron acceptors are preferably applied in the form of a layer to the front of the receiving sheet.

In order to prevent the colour-forming agents, which are contained in the pressure-sensitive recording material, from becoming prematurely active, they are as a rule separated from the electron acceptor substance. This can appropriately be achieved by incorporating the colour-forming agents into foam-like, sponge-like or honeycombed structures. Preferably, however, the colour-forming agents are enclosed in micro-capsules which as a rule can be crushed by pressure.

If the capsules are crushed by pressure, for example by means of a pencil, and if the solution of the colour-forming agent is transferred in this way onto an adjacent sheet which is coated with an electron acceptor, a coloured area is produced. This colour results from the dyestuff, formed during this process, which absorbs in the visible region of the electromagnetic spectrum.

Several processes for the manufacture of micro-capsules have been known for a long time. Known processes are described, for example, in U.S. Pat. Nos. 2,183,053, 2,797,201, 2,800,457, 2,800,458, 2,964,331, 3,016,308, 3,171,878, 3,265,630, 3,405,071, 3,418,250, 3,418,656, 3,424,827 and 3,427,250. Further processes are described in British Pat. Specification No. 989,264 and above all in British Pat. Specifications Nos. 1,156,725, 1,301,052 and 1,355,124. Each of these processes, and other processes, are suitable for encapsulating the colour-forming agents.

The colour-forming agents are preferably encapsulated in the form of solutions in organic solvents. Examples of suitable solvents are preferably non-volatile solvents, for example polyhalogenated diphenyl, such as trichlorodiphenyl, or a mixture thereof with liquid paraffin, and also tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of diphenyl, naphthalene or triphenyl, terphenyls, partially hydrogenated terphenyl or other chlorinated or hydrogenated, fused aromatic hydrocarbons.

The capsule walls can be formed uniformly around the droplets of the solution of the colour-forming agent by means of coacervation forces, it being possible for the encapsulating material to consist of, for example, gelatine and gum arabic, as described, for example, in U.S. Pat. No. 2,800,457. The capsules can preferably also be formed from an aminoplast or modified aminoplasts by polycondensation, as described in British Pat. Specification Nos. 989,264 and 1,156,725.

The micro-capsules containing the colour-forming agents of the formula (1) can be used to manufacture pressure-sensitive copying materials of the most diverse known types. The various systems differ from one another essentially in the arrangement of the capsules and of the colour reactants and in the carrier material.

A preferred arrangement is that in which the encapsulated colour-forming agent is applied in the form of a layer to the back of a transfer sheet and the electron acceptor substance is applied in the form of a layer to the front of a receiving sheet. However, the components can also be used in the paper pulp.

A further arrangement of the constituents is for the micro-capsules containing the colour-forming agent and the developer to be in or on the same sheet in the form of one or more individual layers, or in the paper pulp.

Such pressure-sensitive copying materials are described, for example, in U.S. Pat. Nos. 2,730,457, 2,932,582, 3,418,250, 3,418,656, 3,427,180 and 3,516,846. Further systems are described in British Pat. Specification Nos. 1,042,596, 1,042,597, 1,042,598, 1,042,599, 1,053,935 and 1,517,650. Micro-capsules which contain the colour-forming agents of the formula (1) are suitable for each of these systems and for other pressure-sensitive systems.

The capsules are preferably secured to the carrier by means of a suitable adhesive. Since paper is the preferred carrier material, these adhesives are mainly paper-coating agents, such as gum arabic, polyvinyl alcohol, hydroxymethylcellulose, casein, methylcellulose or dextrin.

The term "paper" used here includes not only normal papers of cellulose fibres but also papers in which the cellulose fibres are replaced (partially or completely) by fibres of synthetic polymers.

The azine compounds of the formulae (1) to (4) can also be used as colour-forming agents in a thermo-reactive recording material. This material as a rule contains at least one carrier, a colour-forming agent, an electron acceptor substance and, if appropriate, also a binder. Thermo-reactive recording systems comprise, for example, heat-sensitive recording and copying materials and papers. These systems are used, for example, for recording information, for example in computers, teleprinters or telex machines, or in measuring instruments. The production of the image (production of the marking) can also be effected manually using a heated pen. Laser beams are a further device for producing markings by means of heat.

The thermo-reactive recording material can be built up in such a way that the colour-forming agent is dissolved or dispersed in a layer of binder and the developer is dissolved or dispersed in the binder in a second layer. Another possibility is for both the colour-forming agent and the developer to be dispersed in one layer. The binder is softened in specific regions by means of heat and at these points, to which heat is applied, the colour-forming agent comes into contact with the electron acceptor substance and the desired colour develops immediately.

The developers are the same electron acceptor substances as are used in pressure-sensitive papers. Advantageously, the developer is solid at room temperature and softens or melts above 50° C. Examples of developers are the clay minerals and phenol resins or phenolic compounds already mentioned, such as, for example, 4-tert.-butylphenol, 4-phenylphenol, 4-hydroxydiphenyl oxide, α-naphthol, β-naphthol, methyl 4-hydroxybenzoate, 4-hydroxyacetophenone, 2,2'-dihydroxydiphenyl, 4,4'-isopropylidenediphenol, 4,4'-isopropylidene-bis-(2-methylphenol), 4,4'-bis-(hydroxyphenyl)-valeric acid, hydroquinone, pyrogallol, phloroglucinol, p-, m- and o-hydroxybenzoic acid, gallic acid, 1-hydroxy-2-naphthoic acid and also boric acid and aliphatic dicarboxylic acids, such as, for example, tartaric acid, oxalic acid, maleic acid, citric acid, citraconic acid or succinic acid.

Film-forming binders which can be melted are preferably used for the manufacture of the thermo-reactive recording material. These binders are usually water-soluble, whilst the azine compounds and the developer are insoluble in water. The binder should be capable of dispersing and fixing the colour-forming agent and the developer at room temperature.

The binder softens or melts under the action of heat, so that the colour-forming agent comes into contact with the developer and can form a colour. Examples of binders which are soluble in water or at least swellable in water are hydrophilic polymers, such as polyvinyl alcohol, polyacrylic acid, hydroxyethylcellulose, methylcellulose, carboxymethylcellulose, polyacrylamide, polyvinylpyrrolidone, gelatine and starch.

If the colour-forming agent and the developer are in two separate layers, binders which are insoluble in water, that is to say binders which are soluble in non-polar or only slightly polar solvents, such as, for example, natural rubber, synthetic rubber, chlorinated rubber, alkyd resins, polystyrene, styrene/butadiene copolymers, polymethyl methacrylates, ethylcellulose, nitrocellulose and polyvinylcarbazole, can be used. The preferred arrangement is, however, that in which the colour-forming agent and the developer are contained in one layer in a water-soluble binder.

The thermo-reactive layers can contain further additives. These layers can, for example, contain talc, $TiO_2$, ZnO or $CaCO_3$, or also organic pigments, such as, for example, urea-formaldehyde polymers, in order to improve the whiteness, to facilitate printing of the papers and to prevent the heated pen from adhering. In order to ensure that the colour is formed only within a limited temperature range, substances such as urea, thiourea, acetanilide, phthalic anhydride or other corresponding fusible products which induce the simultaneous melting of the colour-forming agent and the developer, can be added.

Typical thermo-reactive recording materials, in which the colour-forming agents of the formulae (1) to (4) can be used, are described, for example, in German Offenlegungsschriften Nos. 2,110,859 and 2,228,581, in French Patent Specification No. 1,524,826 and in Swiss Patent Specification Nos. 164,976, 407,185, 444,196 and 444,197.

In the examples which follow, the percentages given relate to the weight unless otherwise stated.

MANUFACTURING INSTRUCTIONS

A. 15.05 g of 4-N,N-dibenzylaminobenzaldehyde and 1.25 g of hydrazine hydrate are stirred in 60 ml of ethanol, with the addition of 5 drops of glacial acetic acid, for 1 hour at 80° C. After cooling to 10° C, the precipitate which has formed is filtered off, washed with ethanol and dried. This gives 14.5 g of a compound of the formula

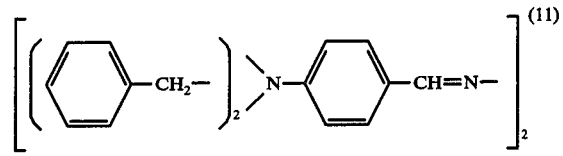

which melts at 192° – 193° C. On silton clay this colour-forming agent develops a yellow-red colour shade.

B. If the 4-N,N-dibenzylamino-benzaldehyde in Manufacturing Instruction A is in each case replaced by equimolar amounts of 4-N,N-dimethylamino-benzaldehyde, 4-N,N-diethylamino-benzaldehyde, 4-N,N-diethylamino-2-methyl-benzaldehyde, 4-ethoxy-benzaldehyde, 2-methyl-3-formylindole, 1-ethyl-2-methyl-3-formyl-indole, 1-benzyl-2-methyl-3-formyl-indole, 3-formyl-9-methyl-carbazole, 3-formyl-9-ethyl-carbazole, 1-n-octyl-2-methyl-3-formyl-indole, 4-N-p-methoxyphenyl-N-methylamino-benzaldehyde, 4-N,N-dimethylamino-2-methyl-benzaldehyde, 4-morpholino-benzaldehyde, 4-N,N-diethylamino-2,6-dichlorobenzaldehyde, 4-N-benzyl-N-ethylamino-benzaldehyde, 4-N-β-chloroethyl-N-ethylamino-benzaldehyde, 4-N-β-hydroxyethyl-N-ethylamino-benzaldehyde or 4-N,N-bis-(β-chloroethyl)-amino-benzaldehyde, and in other respects the procedure is as described in Manufacturing Instruction A, the colour-forming agents of the formulae (12) to (29) listed in the table which follows are obtained.

Table

| Formula No. | (A—CH=N—)$_2$ A | Melting point ° C | Colour on silton clay |
|---|---|---|---|
| (11) | [(C$_6$H$_5$—CH$_2$)$_2$N—C$_6$H$_4$—] | 192–193 | yellow-red |
| (12) | (CH$_3$)$_2$N—C$_6$H$_4$— | 266–268 | yellow-red |
| (13) | (C$_2$H$_5$)$_2$N—C$_6$H$_4$— | 187–189 | yellow-red |

Table-continued
| Formula No. | (A—CH=N—)₂  A | Melting point °C | Colour on silton clay |
|---|---|---|---|
| (14) | 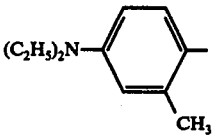 | 186–188 | yellow-red |
| (15) | 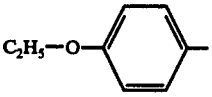 | 173–174 | yellow |
| (16) | 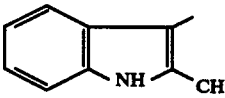 | >310 | yellow |
| (17) | 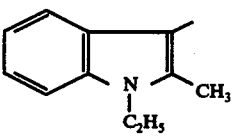 | 241–244 | yellow |
| (18) | 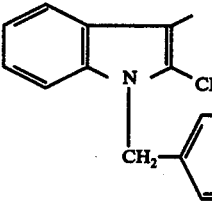 | 304–307 | yellow |
| (19) | 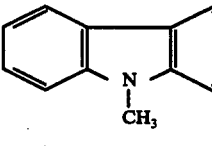 | 308–309 | orange |
| (20) | 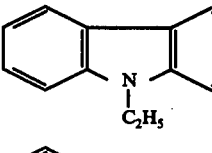 | 244–246 | orange |
| (21) | 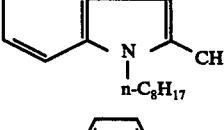 | 150–151 | yellow |
| (22) | 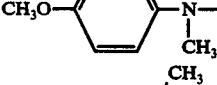 | 199–202 | red |
| (23) | 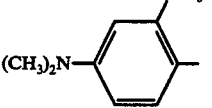 | 207–209 | yellow-red |
| (24) | 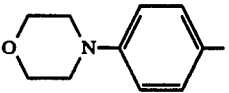 | >245 | yellow-red |
| (25) | 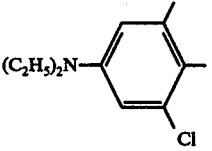 | 227–228 | orange |

Table-continued

| Formula No. | (A—CH=N—)₂ A | Melting point °C | Colour on silton clay |
|---|---|---|---|
| (26) | ![benzyl-ethyl-amino-phenyl] —⟨C₆H₅⟩—CH₂—N(C₂H₅)—⟨C₆H₄⟩— | 164–165 | yellow-red |
| (27) | C₂H₅, Cl—CH₂CH₂ \N—⟨C₆H₄⟩— | 146–148 | yellow-red |
| (28) | C₂H₅, HO—CH₂CH₂ \N—⟨C₆H₄⟩— | 182–185 | yellow-red |
| (29) | (Cl—CH₂CH₂)₂N—⟨C₆H₄⟩— | 163–164 | yellow-red |

EXAMPLE 1

Manufacture of a Pressure-Sensitive Copying Paper

A solution of 3 g of the azine compound of the formula (13) in 97 g of partially hydrogenated terphenyl is emulsified in a solution of 12 g of pigskin gelatine in 88 g of water at 50° C. A solution of 12 g of gum arabic in 88 g of water at 50° C is then added and subsequently 200 ml of water at 50° C are added. The resulting emulsion is poured into 600 g of ice water and the mixture is cooled, whereupon coacervation is effected. A sheet of paper is coated with the resulting suspension of microcapsules and dried. A second sheet of paper is coated with silton clay. The first sheet and the paper coated with silton clay are placed on top of one another with the coatings adjacent to one another.

By writing by hand or with a typewriter on the first sheet, pressure is exerted and a yellowish-tinged red copy, which is outstandingly fast to light, develops on the sheet coated with clay.

Corresponding yellow, orange and red shade effects can be achieved by using each of the other colour-forming agents of the formulae (11), (12) and (14) to (29) listed in the table.

EXAMPLE 2

Manufacture of a Thermo-Reactive Paper

6 g of an aqueous dispersion which contains 1.57% of the azine compound of the formula (12) and 6.7% of polyvinyl alcohol are mixed with 134 g of an aqueous dispersion which contains 14% of 4,4-isopropylidenediphenol, 8% of attapulgite clay and 6% of polyvinyl alcohol. This mixture is applied to a paper and dried. By touching the paper with a heated ballpoint pen, a deep yellowish-tinged red colour is obtained which is outstandingly fast to light.

Similar results are obtained when any of the other colour-forming agents of the formulae (11) and (13) to (29) listed in the table is used.

I claim:

1. A pressure-sensitive and/or heat-sensitive recording material which contains, as the colour former, at least one azine compound of the general formula $$A - CH = N - N = CH - A \quad (1)$$

wherein A represents one of the following radicals

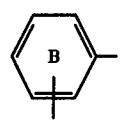

(1.1)

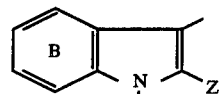

(1.2)

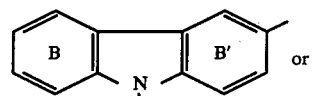

(1.3)

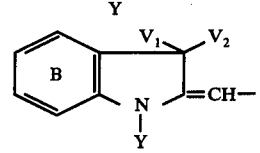

(1.4)

wherein
X represents the radical

—O—R₁ or —S—R₁,

R₁ represents alkyl which has at most 12 carbon atoms and is unsubstituted or substituted by halogen, hydroxyl, cyano, lower alkoxy, lower alkoxycarbonyl, cycloalkyl, or phenyl or benzyl which are unsubstituted or substituted by halogen, nitro, lower alkyl or lower alkoxy, R₂ represents hydrogen, alkyl which has at most 12 carbon atoms and is unsubstituted or substituted by halogen, hydroxyl, cyano, lower alkoxy, lower alkoxycarbonyl, cycloalkyl, or benzyl which is unsubstituted or substituted by halogen, nitro, lower alkyl or lower alkoxy, or R$_1$ and R$_2$ together with the nitrogen atom which links them represent a 5-membered or 6-membered heterocyclic radical, Y represents hydrogen, alkyl which has at most 12 carbon atoms and is unsubstituted or substituted by halogen, hydroxyl, cyano, lower alkoxy, lower alkoxy-carbonyl, or benzyl which is unsubstituted or substituted by halogen, nitro, lower alkyl or lower alkoxy, Z represents hydrogen, lower alkyl or phenyl and V$_1$ and V$_2$ each represent lower alkyl, cycloalkyl or benzyl, or conjointly represent alkylene, and the rings B and B' independently of one another are unsubstituted or substituted by halogen, nitro, cyano, trifluoromethyl, lower alkyl, lower alkoxy, lower alkoxy-carbonyl, phenoxy, amino, lower alkylamino or N-lower alkyl-carbonylamino.

2. A recording material according to claim 1 wherein the colour former corresponds to the formula (1) in which the two A's represent a radical of the formula (1.1), in which X is an amino group

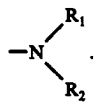

3. A recording material according to claim 1, wherein the colour former corresponds to the general formula $$A_1 - CH = N - N = CH - 0 A_1 \qquad (2)$$

wherein A$_1$ represents one of the following radicals

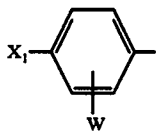 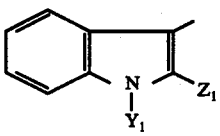

(2.1)    (2.2)

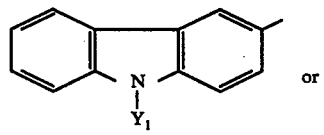

or (2.3)

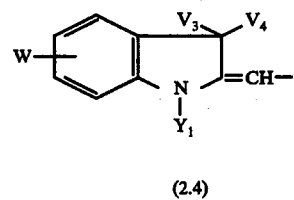

(2.4)

wherein
X$_1$ represents the radical

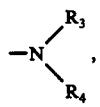

—O—R$_3$ or —S—R$_3$, R$_3$ and R$_4$ independently of one another represent lower alkyl or benzyl which is unsubstituted or substituted by halogen, nitro, methyl or methoxy, Y$_1$ represents alkyl of 1 to 8 carbon atoms, or benzyl which is unsubstituted or substituted by halogen, nitro, methyl or methoxy, Z$_1$ represents lower alkyl or phenyl, V$_3$ and V$_4$ each represent lower alkyl and W represents hydrogen, halogen, lower alkyl or lower alkoxy.

4. A recording material according to claim 1, wherein the colour former corresponds to the general formula $$A_2 - CH = N - N = CH - A_2 \qquad (3)$$

wherein A$_2$ represents one of the following radicals

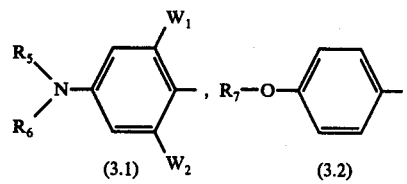

(3.1)    (3.2)

or

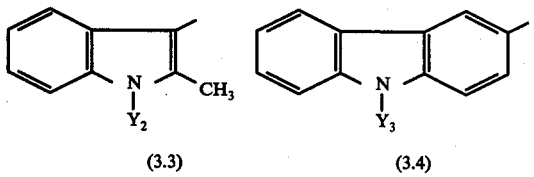

(3.3)    (3.4)

wherein R$_5$ represents lower alkyl, hydroxy-lower alkyl, chloro-lower alkyl, benzyl, phenyl or methoxyphenyl, R$_6$ represents lower alkyl, hydroxy-lower alkyl, chloro-lower alkyl or benzyl, or R$_5$ and R$_6$, together with the nitrogen atom which links them, represent pyrrolidino, piperidino or morpholino, R$_7$ represents lower alkyl, W$_1$ and W$_2$ each represent hydrogen, chlorine or methyl, Y$_2$ represents alkyl of 1 to 8 carbon atoms or benzyl and Y$_3$ represents lower alkyl.

5. A recording material according to claim 3, wherein the colour former corresponds to the general formula

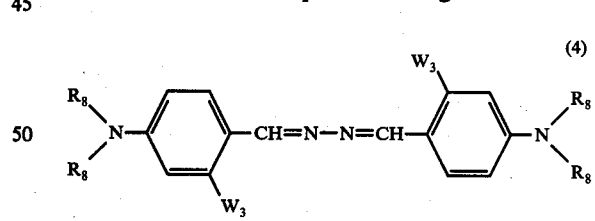

(4)

wherein R$_8$ represents lower alkyl or benzyl and W$_3$ represents hydrogen or methyl.

6. A recording material according to claim 5, wherein the colour former corresponds to the formula (4), in which R$_8$ represents methyl or ethyl.

7. A pressure-sensitive recording material according to claim 1, comprising at least one pair of sheets containing at least one colour former and at least one electron acceptor, wherein the colour former has the formula indicated in claim 1.

8. A pressure-sensitive recording material according to claim 7 which contains at least one colour former of the formula indicated in claim 1, dissolved in an organic solvent and at least one electron acceptor substance.

9. A pressure-sensitive recording material according to claim 8 wherein the colour former, dissolved in an organic solvent, is contained in micro-capsules which can be crushed by pressure.

10. A pressure-sensitive recording material according to claim 7 which contains, as the electron acceptor substance, attapulgite clay, silton clay or a phenol-formaldehyde resin.

11. A pressure-sensitive recording material according to claim 9 wherein the encapsulated colour former is applied in the form of a layer to the back of a transfer sheet and the electron acceptor substance is applied in the form of a layer to the front of the receiving sheet.

12. A pressure-sensitive recording material according to claim 1 which contains the colour former of formula (1) together with one or more other known colour formers.

13. A heat-sensitive recording material according to claim 1 which contains at least one colour former, at least one electron acceptor and at least one binder in at least one layer, wherein the colour former has the formula indicated in claim 1.

14. A heat-sensitive recording material according to claim 13 containing at least one colour former and at least one electron acceptor in at least one binder layer on paper, wherein the colour former has the formula indicated in claim 1.

15. A heat-sensitive recording material according to claim 13, which contains, as the electron acceptor, attapulgite clay, silton clay or a solid organic acid.

* * * * *